United States Patent
Barbreau et al.

(10) Patent No.: US 8,093,067 B2
(45) Date of Patent: Jan. 10, 2012

(54) MAGNETIC IMMUNODIAGNOSTIC METHOD FOR THE DEMONSTRATION OF ANTIBODY/ANTIGEN COMPLEXES ESPECIALLY OF BLOOD GROUPS

(75) Inventors: Yves Barbreau, Mouvaux (FR); Olivier Boulet, Bethune (FR); Arnaud Boulet, Drocourt (FR); Alexis Delanoe, Marcq-en-Baroeul (FR); Laurence Fauconnier, Toufflers (FR); Fabien Herbert, Lille (FR); Jean-Marc Pelosin, Lambersart (FR); Laurent Soufflet, Chateur l'Abbaye (FR)

(73) Assignee: Diagast, Loos (FR)

( * ) Notice: Subject to any disclaimer, the term of this patent is extended or adjusted under 35 U.S.C. 154(b) by 607 days.

(21) Appl. No.: 12/084,507

(22) PCT Filed: Nov. 3, 2006

(86) PCT No.: PCT/EP2006/068085
§ 371 (c)(1), (2), (4) Date: May 1, 2008

(87) PCT Pub. No.: WO2007/051844
PCT Pub. Date: May 10, 2007

(65) Prior Publication Data
US 2009/0269776 A1    Oct. 29, 2009

(30) Foreign Application Priority Data
Nov. 3, 2005  (FR) .................................. 05 11207

(51) Int. Cl.
*G01N 33/553* (2006.01)
(52) U.S. Cl. .................................................. 436/526
(58) Field of Classification Search .................. None
See application file for complete search history.

(56) References Cited

U.S. PATENT DOCUMENTS

| | | | | |
|---|---|---|---|---|
| 4,438,068 A | * | 3/1984 | Forrest | 422/61 |
| 5,318,914 A | * | 6/1994 | Matte et al. | 436/526 |
| 5,753,477 A | * | 5/1998 | Chan | 435/455 |
| 5,770,388 A | * | 6/1998 | Vorpahl | 435/7.25 |
| 6,303,390 B1 | * | 10/2001 | Den Boer et al. | 436/520 |

FOREIGN PATENT DOCUMENTS

| | | |
|---|---|---|
| DE | 4228395 A1 | 8/1992 |
| EP | 0230768 A1 | 8/1987 |
| EP | 0297290 A2 | 1/1989 |
| EP | 0351857 B1 | 11/1994 |

* cited by examiner

*Primary Examiner* — Ann Lam
(74) *Attorney, Agent, or Firm* — Blakely, Sokoloff, Taylor & Zafman

(57) ABSTRACT

The invention relates to a magnetic immunodiagnostic method for the demonstration of antibody-antigen complexes. One such method involves the research and/or identification of antibodies or antigens, preferably anti-antigen antibodies or antigens of a blood group, and comprises a suspension of magnetic particles coated with antigens that can be carried by cells such as erythrocytes. The invention also relates to a device and a kit for carrying out one such method.

30 Claims, 8 Drawing Sheets

Figure 1A:
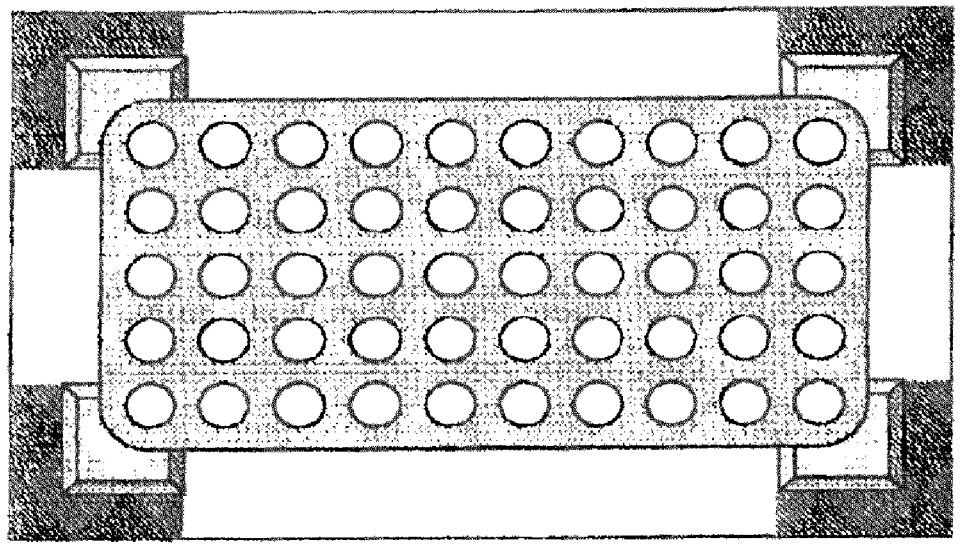

MAGNETIC IMMUNODIAGNOSTIC METHOD FOR THE DEMONSTRATION OF ANTIBODY/ANTIGEN COMPLEXES ESPECIALLY OF BLOOD GROUPS

The present patent application is a non-provisional application claiming the benefit of International Application No. PCT/EP2006/068085, filed Nov. 3, 2006.

The invention relates to a magnetic immunodiagnostic method for the demonstration of antibody/antigen complexes. Ono such method involves the research and/or identification of antibodies or antigens, preferably anti-antigen antibodies or antigens of a blood group, and comprises a suspension of magnetic particles coated with antigens that can be carried by cells such as erythrocytes. The invention also includes a device and kit for carrying out one such method.

At the present Lime, blood transfusion consists in intravenous administration of concentrated red cell preparations (globular concentrates) obtained from donor blood.

The principal risk of blood transfusions is the possibility of bringing together an antibody and its erythrocyte antigen in the recipient's body (person receiving the transfusion). Erythrocyte membrane antigens, notably blood group (or system) antigens, are found at the surface of erythrocytes, also called red cells or red blood corpuscles, which are capable of being recognised by the immune system and triggering an immune response.

Donor red cells are said to be compatible with the recipient's blood if the recipient has no circulating antibodies directed against the donor's erythrocyte antigens.

Among the antigen variants of a erythrocyte membrane antigen that make up blood groups, over twenty erythrocyte antigen systems in humans have been identified to date, the ABO system with A or B antigens, Rhesus system with D, E or e and C or c antigens, Kell system with K or k antigens, Duffy (Fya, Fyb), Kidd (Jka, Jkb) or other less frequently researched systems in practice which also exist such as MNS, Lewis, etc. Individuals with the same combination of erythrocyte antigens belong to the same erythrocyte blood group. Blood groups become even more complex and numerous when several antigen systems are used.

With the exception of pathological conditions, in the case of an autoimmune disease for example, an individual's serum can contain two types of antibodies directed against erythrocyte antigens:

(i) so-called regular antibodies directed against antigens of the ABO system (for example anti-A antibodies in group B individuals). These are IgM type immunoglobulins which are, capable of agglutinating red cells in vitro. This phenomenon is useful in establishing the ABO group of an individual using the Beth-Vincent and Simonin tests. The Beth-Vincent test makes it possible to determine which antigens are carried by red cells (antigen phenotype) and the Simonin test makes it possible to carry out a complementary study, in other words to detect anti-A and and/or anti-B antibodies circulating in an individual's serum.

In the Beth-Vincent test, an individual's red cells are contacted with test serums, or test antibodies, each of which has a particular antibody type directed against an antigen of the ABO system. This is therefore a test of the agglutination of serum with test red cells.

In the Simonin test, also called a counter-test, an individual's serum containing these circulating antibodies is contacted with the test red cells, or test erythrocyte, each of which belongs to a specific antigen group of the ABO system. This is therefore a Lest for the agglutination of serum to the test red cells, (ii) so-called irregular (or immune) antibodies whose presence in the serum of plasma is optional and which are directed against antigens of non-ABO systems. This most commonly involves IgG, which appears following antigen stimulation by foreign red cells, for example following immunisation against one or more antigens in the course of blood transfusions, or even during pregnancy as a result of a maternal immune reaction against foetal erythrocyte antigens not belonging to the mother's blood group, notably during birth.

Researching these irregular antibodies is called irregular agglutinin research (IAR). This test is used to detect the presence or otherwise in the blood of an individual of IgGs directed against various erythrocyte antigens. To carry out this test, binding of these IgGs to the test red cells whose antigens are known is researched. This method is carried out simultaneously on many types of red cells and comparison of the results makes it possible to identify the IgG(s) present.

The risk is greater for the most immunogenic antigens, such as rhesus D, but also for other rhesus types (E>c>e>C), Kell (K), Duffy (Fy a, Fy b), Kidd (Jka, Jkb), etc.

In practice, it is not possible to take into consideration all these antigens when carrying out a transfusion, as obtaining the right blood group at the right moment would not be possible, especially as some antigenic combinations are extremely rare. Standard transfusions only take into account the ABO group plus rhesus D (Rh+ or Rh−) In situations where there is a risk of an irregular agglutinin, a number of other systems are taken into consideration, notably rhesus C and E and Kell, and at times other systems. Therefore, for these risk situations, it is important to ensure compatibility of the donor's blood group with that of the recipient's blood group by taking into account the presence or risk of occurrence of these irregular agglutinins.

Thus, in recipient patients with irregular anti-erythrocyte antibodies or in a risk situation, for example patients receiving multiple transfusions but not having anti-erythrocyte irregular antibodies and in pregnant women, it is vital to select erythrocyte concentrate units which are transfused in such a way that the donor's red cells are devoid of antigens against which the recipient's antibodies are directed or likely to appear. This compatibility test is compulsory in these patients and is used preventively in all recipients prior to administration of erythrocyte concentrates by means of a direct compatibility test with the donor's red blood cells in the presence of recipient serum or plasma. No agglutination reaction and/or lysis reaction in the techniques used in IAR should be found In clinical transfusion practice, the erythrocyte phenotype, which corresponds to research and identification of the antigens of the blood group at the surface of red blood corpuscles (with the exception of the ABO system in which the presence of the corresponding regular antibodies is also researched), concerns both the recipient and donor.

For the recipient and donor, three levels of erythrocyte phenotype exist in order to provide the recipient with compatible erythrocyte concentrates as a function of risk situations:

determination of ABO group phenotype (or ABO group) and standard rhesus (presence or absence of antigen D), determination of Kell rhesus phenotype (presence or absence of antigen C, E, c, e and K), and determination of extended (or larger) phenotypes (presence or absence of antigens of the Duffy system, Fy a and Fy b system, Kidd system, Jk a and Jk b and of the MNSs system (antigens S and s), other antigens possibly being researched depending on the type of risk and/or irregular antibodies found in the recipient's serum.

The commonly used techniques used to research and identify the presence or absence of blood group antigen at the surface of the recipient and/or donor erythrocyte, or aimed at researching and identifying the presence or absence of anti-antigen antibodies of the blood group, regular (for ABO group) or irregular in the case of IAR in the serum or plasma of the donor and/or recipient, are well known to the man skilled in the art and will not be described here.

In phenotyping, they generally consist of researching the presence or absence of the antigen in question using test serums Containing the appropriate antibodies. Preferably, the antibodies contained in these test serums are agglutinants (IgM or IgA) which makes it possible to obtain total or partial agglutination of the erythrocytes whose phenotype is being researched when the latter carries the antigen corresponding to the antibody present in the test serum. However, it is possible to use non-agglutinant test antibodies (of the IgG type) in which agglutination is triggered by an anti-immunoglobulin and becomes visible after a centrifugation step and resuspension of the residue obtained (known as the Coombs indirect technique). It is also possible to use non-agglutinant test antibodies where the presence of these test antibodies bound to the red cells is visualised by means of an anti-immunoglobulin bound to a solid phase (immunoadhesin technique). Results are read with the naked eye or by means of an appropriate device.

For research or identification, in a sample of the patient serum or plasma to be tested, of blood group anti-antigen antibodies, regular for the ABO or irregular for IAR, test erythrocytes (also called red blood corpuscles or test red blood cells 5) are contacted with the patient's serum or plasma of known antigenicity for a number of blood group systems (ABO, rhesus, Kell, Duffy, Kidd, MNSs, etc. In the case of IAR, for which the antibodies likely to be present are more likely to be non-agglutinant, the technique used is indirect Coombs by agglutination using anti-immunoglobulin or by immunoadhesin to a solid phase coated with an anti-immunoglobulin.

For IAR, a first step involves the use of a panel of red cells, this is called screening (two or three red cells from different groups selected so as to include the maximum number of antigens) and makes it possible to detect (but not to identify) the presence or absence of irregular antibodies. When screening is positive, identification of the specificity of the irregular antibodies present is carried out by means of a panel of red cells, called identification red cells, and including 10 different phenotyped red cells in the vast majority of known blood group systems.

There exists a large number of variations of the techniques used for phenotyping or IAR in the field of blood transfusions These techniques may be manual, on microplates, in tubes or in microplate cupules, or fully automated by means of a sample distributor and reagent, stirrer, incubator and automatic reading with software adapted to the technique used.

The techniques used include techniques where the presence of anti-antigen antibodies of the blood group or antigens of the blood group is based on demonstration of agglutination of red cells after centrifugation using a transparent mini-filtration column (Sephadex® gel or microbeads) where the opening at the upper end acts as an incubation chamber and for which the cut-off threshold selected for the column prevents agglutinated red cells after centrifugation from passing through the column (see in particular patent EP 0 194 212 or patent EP 0 755 719).

We can also cite techniques where phenotyping or IAR is based on demonstration of red cells sensitised with an antibody after centrifugation, followed by immunoadhesion using a separation barrier consisting of a gel or liquid whose density is selected such that only 5 red cells can cross this barrier during centrifugation, with the reaction container being coated in the lower area with an anti-immunoglobulin in order to trap sensitised red cells and give a characteristic image. Among these techniques, we can cite patent document EP 0 058 780 which describes a blood phenotyping method in which the reaction mixture is centrifuged through a high density medium (such as a bovine albumin or polyvinyl pyrrolidone type solution). This has the advantage of eliminating the washing step for sensitised red blood corpuscles. We can also cite patent document WO 98/02752 which describes a general method for determining the presence of a blood antigen on the erythrocytes or of an antibody which binds to such an antigen. In this method, erythrocytes, whether sensitised or not, are separated from non-bound antibodies by centrifugation by means of a separation medium whose density is greater than that of the liquid containing the antibodies but lower than that of the erythrocytes, with sensitised erythrocytes being separated front non-sensitised erythrocytes on the lower wall of the reaction container on which is immobilised an anti-immunoglobulin, and non-sensitised erythrocytes being collected at the base of the container. Analysis of the final image obtained is specific to the presence or otherwise of the test analyte.

Among the variants of the techniques used for phenotyping or IAR, we can also cite those which have been generally developed to research, in a sample, an analyte capable of binding to a cell using magnetic particles, this in particular in order to eliminate centrifugation, a process required in agglutination-based techniques such as the anti-globulin technique (Coombs indirect method by agglutination or immunoadhesion to a solid phase) for IAR or phenotyping. This is also the case, as for IAR, when it is necessary to wash sensitised red cells in order to eliminate non-specific antibodies capable of recognising the anti-immunoglobulin used in the subsequent step.

The centrifugation step is in fact always difficult to carry out in methods that are to be fully automated, notably dun to the cost and cumbersome nature of centrifuges, their handling, etc.

Magnetic particles have been used for many years for the detection of complexes of the ligand-receptor or antibody-antigen type. We can cite the methods described in the following patent documents for example:

document WO 92/17781 which describes a method for determining the presence of a ligand in a sample in which magnetic latex particles are incubated, which may be of different colours, coated with a substance such as an antibody capable of binding to the ligand. This is followed by application of a magnetic field to the incubation medium and, finally, observation of the presence or absence of agglutination, or document EP 0 426 170 which describes a method for determining the presence of ligands in a sample in which magnetic gelatine particles sensitised with antigens or antibodies capable of binding to this ligand are incubated. This is followed by application of a magnetic field to the incubation medium and, finally, observation of the presence or absence of agglutination, said method being characterised in that the manner in which these particles slide is observed after inclining the container, notably in the couple of a microplate with a V-shaped base.

Such magnetic particles have already been used in immunohaematology for phenotyping and/or IAR. The following can be cited as documents describing such applications, document EP 0 351 857 which describes an immunological assay method using magnetised markers such as antibodies or antigens fixed to magnetic latex beads. These markers are capable of binding to a substance which is to be determined in an immunoreaction step. The labelled magnetic particles are then collected in a predetermined region on the surface of a wall in the measurement container using a magnet positioned under this cupule and under the effect of a magnetic field. This method can include a substance which can bind specifically to the substance to be determined which is immobilised on a predetermined region of the surface of the wall in the measurement container. A description exists of an IAR technique by immunoadhesion in which erythrocytes previously fixed to the base of a microplate cupule are sensitised with the recipient's serum then washed (by aspiration and injection of the washing liquid). After this, magnetic latex beads are added to the cupule coated with anti-immunoglobulin prior to application of a magnetic field.

document EP 0 528 708 describes a detection method by immunoadhesion of a biological substance likely to be present in the sample. In this method, the erythrocytes to be phenotyped or used as a screening and/or identification panel undergo preliminary fixing to the base of a microplate. After sensitisation of the fixed erythrocytes with test serum (for phenotyping) or recipient serum to be tested (for IAR), the cupule are washed and magnetic latex beads coated with anti-immunoglobulin are then added. In this method, two types of magnetic fields are applied successively (vertical and circular) in order to displace magnetic particles not specifically bound to the test substance, and patent document EP 0 230 768 describes a co-aggregation method for magnetic particles capable of binding to a substance contained in a sample by means of polycationic compounds or polyanionic compounds in the presence of a magnetic field. In particular, this document describes the separation of plasma in a sample of whole blood containing red cells in which the method involves sequential addition to a container placed on a magnet of the whole blood sample and a Ferrofluid ($FeCl_2/FeCl_3$) coated with succinylated bovine serum albumin, aggregates of the erythrocyte particles obtained in this way are then drawn towards the magnet, thus making it possible to collect plasma clarified by decantation. This document also describes a method for quantification of anti-RH antibodies (anti-D) in a plasma sample, prepared according to the preceding method, which is incubated in the presence of a suspension of fluorescent RH+ red cells and to which mixture is added succinylated ferrofluid and polybrene in a sequential manner, with the red cells being washed several times by application of a magnetic field and decantation prior to the addition of an anti-immunoglobulin. The quantification of anti-RH antibodies in the plasma sample is evaluated by comparison with controls by analysing fluctuations in the amount of fluorescence observed in a given volume.

Thus, it would be useful to have available a quick and simple method for the detection of the presence of an antibody specifically directed against a given antigen in a complex reaction mixture containing antibodies directed against other antigens, in which method there is neither a washing step nor a centrifugation step. Such a method without a centrifugation step and without a washing step, notably for IAR, presents the advantage of being usable on a practical and available support, such as a microplate, of being fully automated.

This is precisely the object of the invention.

In a microplate cupule type reactor with a round base and an inclined wall coated with an anti-immunoglobulin capable of specific binding to an antibody, the inventors have developed a simple and effective method for the detection of a specific complex formed between an antibody and an antigen in a complex reaction mixture that can contain free antibodies, notably directed against other antigens, which is without a washing or centrifugation step. This method uses a suspension of magnetic particles coated with antigen that can be carried by a cell, a method which can be largely automated and applied in particular to TAR and, if need be, to phenotyping of red blood corpuscles.

In this method, the presence of an antibody/antigen complex is determined at the end of the reaction by visualization of the presence of the complex formed on the inclined wall of the reactor as a result of immunoadhesion.

The inventors have surprisingly found that it is possible, following incubation of a reaction mixture consisting of an antibody solution and a suspension of magnetic particles coated with antigens, notably erythrocytes, said reaction mixture being formed in a cupule above a viscous solution or a gel whose density is greater than that of the antibody solution, to migrate said suspension of magnetic particles through this viscous solution or this separating gel towards the inclined wall coated with anti-immunoglobulin and/or the base of the cupule by means of a magnetic field obtained using a magnet located below the cupule followed by visualization of the presence of the specific complex formed by immunoadhesion, and this without causing free antibodies likely to saturate the anti-immunoglobulin to migrate.

Even more surprisingly, the inventors have found that it is possible to improve this method by means of the combined and simultaneous effect of a magnetic field and rotary stirring of the cupule which not only greatly facilitates the migration of particles, particularly coated erythrocytes, through the viscous solution or gel but also to increase the probability of the antigens carried by the magnetic particles encountering the anti-immunoglobulin bound to the inclined wall and cupule base.

While it has been shown that it is possible to use viscous solutions or gels having a density greater than that of the fluid containing the antibodies but lower than that of the erythrocytes to separate by means of centrifugation the erythrocytes (sensitised or otherwise) from free antibodies not bound to these erythrocytes in order to eliminate the washing step in immunoadhesion techniques (refer to previously cited patent documents EP 0 058 780 and WO 98/02752), the inventors have found that it is equally possible to eliminate this centrifugation step by using these viscous substances or gels with magnetic particles carrying the antigen, notably erythrocytes, by means of a magnetic field created by a permanent magnet located externally below the cupule, in particular by combining this magnetic field with a rotary stirring step in the reactor.

Thus, in a first embodiment, the object of the invention is a method for the demonstration of a specific complex formed by reacting an antibody present in a solution and an antigen bound to a magnetic particle, the reaction taking place in a reactor with an open top and sealed base whose diameter decreases in the area close to the base in such a way that it forms an inclined wall extending down to the base, said inclined wall being at least partially coated with an anti-immunoglobulin or any other compound capable of binding to the antibody of said formed complex, wherein it consists of the following steps:

a) Prior to the reaction,
preliminary filling of the reactor with a viscous substance or homogeneous gel such that at least part of the inclined wall of the reactor is coated, b) contacting the solution containing or likely to contain said antibody with the magnetic particle suspension carrying or likely to carry said antigen at a point above the viscous solution in the reactor, c) incubation of the reactor, preferably for a period of time and at a temperature suited to formation of the complex, preferably for at least five minutes, d) application of a magnetic field to said reactor and stirring of the reactor such that the magnetic particles are either drawn towards the base and/or inclined wall of the reactor coated with an anti-immunoglobulin or any other compound capable of binding to the antibody, in particular in such a manner that the vast majority of magnetic particles are found at the base of the reactor and/or specifically bound to the inclined wall by said anti-immunoglobulin or said other compound capable of binding to the antibody, and e) reading with the naked eye and/or by any other suitable reading system of the image obtained at the base of the reactor and/or inclined wall of the reactor coated with said anti-immunoglobulin, the image obtained thus making it possible to demonstrate the presence or otherwise of a specific antibody/antigen complex.

The terms "specific complex formed by reacting an antibody present in a solution and an antigen bound to a magnetic particle" refers, in this description, to the complex formed between an antibody capable of specifically recognizing an antigen and this antigen, this complex being formed on the magnetic particle to which the antigen is bound.

The term "specific complex" also includes the complex formed between an antibody capable of specific recognition of an antigen carried by a cell, notably an erythrocyte, and this antigen, this complex also being formed here on the magnetic particle to which the cell carrying the antigen is bound.

In general, the antibody of the specific antibody/antigen complex can be IgG, IgM, IgA, or IgE or any other category of antibody.

The term "anti-immunoglobulin capable of binding to the antibody of said formed complex" refers here to anti-immunoglobulins, polyclonal or monoclonal, capable of recognising and binding any antibody, particularly human, whether IgG, IgM, IgA, or IgE (total anti-immunoglobulin), or certain specific categories of antibody, notably specific anti-IgG antibodies. Such anti-immunoglobulins, particularly human, are well known to the man skilled in the art and are available from many suppliers and will therefore not be described in detail here, especially in terms of their manufacturing processes.

The term "any other compound capable of binding to the antibody of said formed complex" refers in particular to protein A type compounds or protein G type compounds, well known to the man skilled in the art, for the recognition and specific binding of antibodies.

The term "vast majority of magnetic particles" refers here to at least 60% of the quantity of magnetic particles in the reaction mixture, preferably at least 70%, 80%, 85%, 90% and 95%, even more preferably at least 98%.

In particular, when the antigens are carried by cells, notably erythrocytes, the term "vast majority of magnetic particles" refers to the vast majority of magnetic particles or the vast majority of cells, the vast majority of cells signifying at least 60% of the quantity of magnetised cells present in the reaction mixture, preferably at least 70%, 80%, 85%, 90% and 95%, even more preferably at least 98%.

In the particular case where antigens are carried by cells, notably erythrocytes, step d) concerning application of a magnetic field to said reactor and stirring of the reactor should be such that the magnetic particles or magnetised cells are drawn towards the base and/or inclined wall of the reactor coated with an anti-immunoglobulin or any other compound capable of binding to the antibody, in particular in such a way that the vast majority of magnetic particles or magnetised cells are found at the base of the reactor and/or specifically bound to the inclined wall by said anti-immunoglobulin or said other compound capable of binding to the antibody.

In a preferred embodiment, the invention includes a method according to the invention wherein the reaction mixture, obtained after incubation of a mixture of the solution containing or likely to contain said antibody and magnetic particle suspension carrying or likely to carry said antigen, contains free antibodies, in particular not directed against antigens carried by the magnetic particles, these free antibodies being capable of binding to the anti-immunoglobulin or to the compound used which is capable of binding to the antibody being researched.

The term "free antibodies" refers here to antibodies not forming complexes with an antigen carried by the magnetic particles.

In an equally preferred embodiment, the present invention includes a method according to the invention characterised in that said antibody, contained or likely to be contained in the solution whose formation of a specific complex with an antigen carried by the magnetic particles, is an antibody of IgG type, or if this antibody is an blood group antigen antibody, is a non-agglutinant antibody, the erythrocytes carrying the corresponding antibody.

Even more preferably, when this antibody is of the IgG type, an anti-IgG is the preferred anti-immunoglobulin, notably human anti-IgG (directed against antibodies of human origin).

In a particularly preferred embodiment, the present invention includes a method according to the invention wherein in step d), the reactor is stirred in the presence of a magnetic field.

In step d), The magnetic field application step and reactor stirring step can be carried out starting with one or other of the steps but in such a way that application of the magnetic field and stirring take place simultaneously for at least a given period of time.

Evidently, also included in the method according to the invention is a variation of the method according to the invention in which application of the magnetic field is carried out prior to stirring of the reactor in step d) of the method, with application of the magnetic field alone (without stirring) not exceeding a period of two minutes at the most, preferably one minute 30 s, one minute, or 30 s. This is also the case when stirring is carried out prior to application of the magnetic field, whereby the stirring period alone does not exceed a duration of 2 minutes at the most, preferably 1 minute 30 s at the most, 1 min, or 30 s.

In a particularly preferred embodiment, the present invention includes a method according to the invention wherein in step d), application of the magnetic field is carried out simultaneously with stirring of the reactor.

The term "simultaneously" refers to a period of time not exceeding 20 s where only stirring or only application of a magnetic field is carried out.

With regard to this aspect, the invention includes a method according to the invention wherein in step d), application of the magnetic field and stirring are carried out simultaneously for a period of time ranging from 2.5 min to 10 min.

In a preferred embodiment, the present invention includes a method according to the invention wherein in step d), application of the magnetic field and stirring are carried out simultaneously for a period of time ranging from 4 min to 7 min, even more preferably from 5 min to 6 min.

The present invention includes a method according to the invention wherein in step d), application of the magnetic field is carried out by moans of a magnet located externally below the reactor such that The magnetic particles are drawn towards the base of the reactor, preferably along the longitudinal axis of the reactor.

In a preferred embodiment of the method of the invention, in step d) said magnet is a permanent magnet of magnitude ranging from 8000 to 16000 Gauss, preferably from 10000 to 14000 Gauss, more preferably still from 11500 to 12500 Gauss, with a magnitude of 12000 Gauss being the most preferred.

In a preferred embodiment, the present invention includes a method according to the invention wherein in step d) stirring is carried out by means of a rotary stirrer.

Figure 1B:
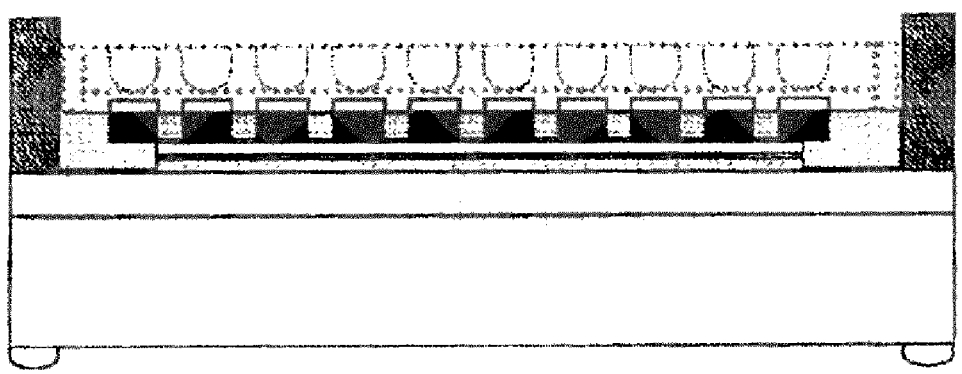

The term "rotary stirrer" refers here in particular to a rotary platform with an amalgamated reactor, or set of reactions in the case of a 96-cupule microplate (refer to FIGS. 1A and 1B).

In a particular mode of stirring, the present invention includes a method according to the invention wherein in step d), stirring consists of rotary stirring having an orbit in a proportion between 1.0 mm and 2.5 mm diameter, preferably between 1.25 and 2.25 mm, between 1.5 mm and 2 mm diameter, with 2 mm being the preferred orbit diameter when the reactor has a diameter of 7 mm at its widest point.

The term "proportion" signifies that, for example when the diameter of the widest section is double or half of 7 mm, the corresponding diameter of the rotation orbit mentioned will be doubled or divided by two.

The term "orbit for rotary type stirring" refers to the diameter of the circle described by the lowest point of the reactor in the course of the stirring process (lowest point 5 of the reactor's longitudinal central axis).

In a preferred embodiment, the present invention includes a method according to the invention wherein in step d), stirring is carried out at a rate between 250 and 750 rpm, preferably between 400 and 600 rpm.

In a particular embodiment, the magnet located between each of the reactors forms part of the stirring platform (see also FIGS. 1A and 1B).

In the latter case, the longitudinal central axis of the magnet located under the reactor follows the orbit formed by the longitudinal central axis of the reactor during stirring.

In a particular embodiment, the magnet located under each of the reactors is not fixed to the stirring platform. In this case, the longitudinal central axis of the magnet located under the reactor does not move and does not follow the orbit formed by the longitudinal central axis of the reactor during stirring.

The present invention includes a method according to the invention wherein in step c), the duration of incubation is between 10 minutes and 30 minutes, preferably between 15 and 25 minutes.

In a preferred embodiment, the present invention includes a method according to the invention wherein in step c), incubation is carried out at a temperature between 10° C. and 40° C., preferably between 25° C. and 40° C., between 30° C. and 40° C., preferably around 37° C. (37° C.±1° C.).

In a preferred embodiment, the present invention includes a method according to the invention wherein in step b), incubation is carried out at a temperature between 30° C. and 40° C., preferably at 37° C.

Immunodiagnostic, capture and tri cellular techniques involving magnetic particles have been the subject of numerous publications and are well known to the man skilled in the art.

Among these techniques, we can cite those making use of the functionalisation of a magnetic particle, thus making it possible to obtain a reactive group on the surface capable of reacting, under appropriate conditions and with suitable reagents, with the antigens that are to be grafted covalently to the particle, notably an acid group, amine group, epoxy or aldehyde group to site but the most common.

We can also cite those techniques making use of passive adsorption of the antigen that is to be bound to the particle, notably by adequate treatment allowing positively or negatively charged beads, depending on the antigen and conditions under which this passive adsorption is to be carried out.

Suppliers of magnetic microbeads (or particles) suitable for use within the scope of the present invention include in particular Ademtech (33600 Pessac, France), who supply magnetic particles with a diameter of around 100 to 500 nm which can be functionalised by an acid or amine, as well as protocols and reagents which make it possible to carry out the desired grafting with these groups. This company also supplies these non-functionalised particles of the hydrophobic type with a diameter of about 300 nm±30 nm, particles used mainly in the examples given below. These magnetic particles consist of over 50% of a ferromagnetic core (such as iron oxide), with this core being coated with polystyrene. Other companies also include Bioclone Inc. (San Diego, Calif., U.S.A.) which supplies a whole range of functionalised magnetic beads. In addition, there is also Dynal Biotech GmbH (Hamburg, Germany) with its wide range of Dynabeads™, which offers in particular magnetic microbeads activated with streptavidine, tocyl or a carboxylic acid group. Another company that can be cited is Merck Chimie SAS (94126 Fontenay sous-Bois, France) which has the Estapor™ range of magnetic microbeads with different particle sizes (300 nm to 2 μm) based on polystyrene or divinylbenzene containing up to 50% ferrites and which can be functionalised or not, for example by an acid or amine group. These particles are prepared by a method using polymerisation of styrene in the presence of a ferromagnetic compound. Finally, we can cite the magnetic particles described in European Patent EP 0 038 730 (Rhône Poulenc) which describes magnetic polymer latex, European Patent EP 0 125 995, European Patent Applications EP 0 105 714, EP 0 190 006, EP 0 238 353 and EP 0 249 357 (Serono Diagnostics) or in French Patents FR 2 262 805 and FR 2 454 098 (Corning Glass Works).

The term "magnetic particles" in the context of the present invention also refers here to ferrofluid aqueous solutions obtained from a mixture of Fe(III) polyoxoanaions and at least a metal M(II) with II degree oxidation, such as Fe(II), a ferrofluid such as that obtained, in particular, by the methods described in examples 1 to 8 of French Patent FR 2 461 521.

Preferably, the ferrofluid solution which can be used in the methods of the invention result from a dilution of a ferrofluid solution obtained by the ferrofluid preparation methods described in examples 1 to 8 of French Patent Application No. 2 461 521, in an aqueous medium and preferably in the absence of a surfactant (or detergent) in order to avoid lysis of the erythrocytes when the latter are contacted with this ferrofluid solution in order to be magnetised, and this in a particularly preferred method of the invention which uses antigens carried by erythrocytes.

In a preferred embodiment, said ferrofluid solution is characterised in that it is prepared from a mixture consisting of Fe(III) polyoxoanions and at least one metal M(II) with an oxidation degree of II, preferably chosen from the first series of transition metals such as Fe(II), Co(II), Mn(II), Cu(II) or Ni (II).

In particular, the ferrofluid solution can be prepared from a mixture of Fe(III) polyoxoanions and at least one metal M(II) combined with a cation such as $H^+$, $CH_3^+$, $N(CH_3)_4^+$, $N(C_2H_5)_4^+$ or any other cation capable of conferring greater solubility in water on the polyoxoanion than the $Na$, $K^+$ and $NH_4^+$ cations. These cations can be carried by suitable acids such as HCL, $CH_3COOH$ or even by the hydroxide of tetramethyl or tetraethyl ammonium.

Preferably, the starting metal sources chosen for FE(III) and M(II) to prepare the ferrofluid will be salts chosen from among:

for Fe(III), those listed in published French Patent No. 2 461 521, page 4, lines 1 and 2, notably ferric chloride, and for M(II), those listed in published French Patent Application No. 2 461 521, page 4, lines 3 to 6, notably ferrous chloride.

Preferably, the ferrofluid solution is prepared from a mixture of Fe(III) and the metal M(II) characterised in that the initial molar ratio of degree II is 2±1, preferably 2±0.5, 2±0.25 or even 2±0.1, the initial molar ratio of 2 between Fe(III) and the metal M(II) of degree II being the most preferred.

Still more preferably, a suitable strong base, such as sodium hydroxide, tetramethyl or tetraethyl ammonium hydroxide, is added to the initial mixture of Fe(III) and metal M(II) salt.

Preferably still, the ferrofluid aqueous solution undergoes preliminary dilution in a buffer or saline solution.

In certain applications, in particular when sensitivity or the rate of reaction is to be improved (but without increasing the non-specificity of the test), it is possible to use a low ionic strength buffer (ISB), also called LISS buffer.

In a preferred embodiment, said ferrofluid solution is diluted to 0.25 to 10% (v/v) in said buffer or said saline solution, preferably between 0.25 and 5%, between 0.25 and 2.5%, between 0.25 and 1%, and between 0.25 and 0.75%.

In a preferred embodiment, the present invention includes a method according to the invention wherein the magnetic particles have a diameter between 100 nm and 1.5 µm, preferably between 150 nm and 1.2 µm, between 200 nm and 1 µm or between 200 nm and 800 nm, the latter being the most preferred.

In a preferred embodiment, the present invention includes a method according to the invention wherein the magnetic particles contain at least 35%, preferably at least 50% by weight of ferromagnetic compound (ferrite or iron oxide for example), preferably at least 70%, said ferromagnetic compounds preferably being iron oxides.

Even more preferably, when the antigen of the specific complex is carried by a cell, notably an erythrocyte, the magnetic particles are hydrophobic and undergo preliminary washing in the presence of a surfactant, preferably a nonionic detergent.

In a preferred embodiment, the present invention includes a method according to the invention wherein in step a), preliminary filling of the reactor with a viscous substance or homogeneous gel is carried out using a viscous substance or gel whose density is such that it prevents the migration of antibodies which do not form complexes with the antigens bound to the magnetic particles towards the inclined wall and the base of the reactor coated with anti immunoglobulin or compounds capable of recognising antibodies during step d).

In a preferred embodiment, the present invention includes a method according to the invention wherein in step a), the viscous solution or gel has a density greater than 1. Preferably, the viscous solution is based on serum albumin, in particular bovine, or polyvinyl pyrrolidone (PVP-40 or PVP 60) or even gelatine.

The man skilled in the art will have the necessary knowledge to adapt the protocol described below in the examples for a homogeneous superfine Sephadex™ G-100 gel solution to other types of gel or viscous solution, depending on the nature of the antigens (carried or by cells or not), and size and composition of ferrite magnetic particles, in order to obtain complete migration of the particles through these viscous solutions or gels, notably by varying the final density of the viscous solution or gel, migration time (stirring), stirring speed and, if need be, rotation orbit of rotary stirring.

For example, with regard to the viscous solution based on albumin or PVP, concentrations in the region of 30%±10% can be used.

In a preferred embodiment, the present invention includes a method according to the invention wherein in step a), the gel is dextran or agarose (Sepharose™ (Pharmacia, Sweden), namely Sepharose™ 4B or 6B).

In an equally preferred embodiment, when said solution is of the gel type, this gel is prepared in the presence of bovine serum albumin in order to increase the density of the gel solution, preferably to final concentrations in the gel solution of 5% to 15% w/v, preferably 10%±2.5%.

In a preferred embodiment, the present invention includes a method according to the invention wherein in step a), the viscous solution or gel is Sephadex™, (Pharmacia, Sweden, or Sigma-Aldrich), preferably G-10™, G-25™, G-50™, G-75™, G-100™, G-150™ or G-200™, where the diameter of the dextran beads can range from 20 nm to 300 nm. More preferably, Sephadex™ is superfine G-100™.

Even more preferably, gel concentration, particularly that of Sephadex™ or Sepharose™ is between 1.5% and 6%, preferably between 2% and 5%, between 2.5% and 4%. A concentration of 3%±0.5% is the most preferred, notably for Sephadex™, in particular for superfine G-100™.

In a preferred embodiment, the present invention includes a method according to the invention wherein in step b), said solution containing or likely to contain said antibody is deposited on the viscous solution prior to depositing the magnetic particle suspension carrying or likely to carry said antigen.

In a preferred embodiment, the present invention includes a method according to the invention wherein prior to step b), the viscous solution or gel is coated with an aqueous solution in order to dilute the reaction mixture deposited in step b), preferably when the antibody solution is non-diluted human serum or plasma. Preferably, said aqueous solution used to dilute the antibody solution or sample represents a volume that is 1 to 10 times the volume of the antibody solution, preferably still 2 to 7 times the volume, 3 to 6 times the volume or 4 to 5.5 times the volume. A 4 to 5 times volume is the most preferred range, notably in a 96-well type microplate cupule. The dilution solution can thus be saline solution which can also contain BSA (see below for preferred BSA concentrations).

In a preferred embodiment, the present invention includes a method according to the invention wherein prior to step b), the viscous solution or gel is coated with an aqueous solution also in order to prevent direct contact of the sample containing the test antibodies (plasma or serum) with the wall of the cupule coated with HAG or to prevent mixing of this sample with the viscous solution or gel, this in order to prevent any reaction or saturation of coated HAGs at the base of the wall with non-specific antibodies contained in said plasma or serum sample, since reaction or saturation would prevent later binding of the specific antibody/antigen complex that is to be detected.

Figure 2A:
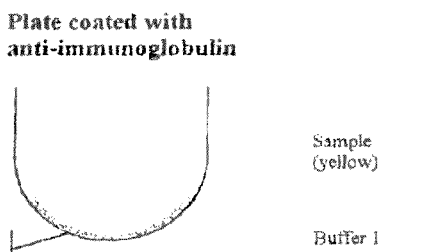
Figure 2B:
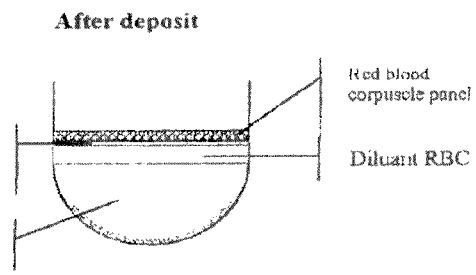

In a preferred embodiment, the present invention includes a method according to the invention wherein prior to step b), the viscous solution or gel is coated with an aqueous solution in order to dilute and encourage the formation of antibody/antigen complex in step b) (see FIGS. 2A and 2B)

In this case, where a specific complex formed by an antibody/antigen of a blood group is to be demonstrated, notably within the context of IAR or red corpuscle phenotyping, this diluted solution encourages the reaction which is carried out using a low ionic strength buffer (ISB), this buffer being known to the man skilled in immunohaematology. This low ionic strength buffer being ISB, if need be, obtained in the presence of a final bovine serum albumin (BSA) concentration between 1.5% and 6% (w/v), preferably between 2% and 5%, with a value of 3%±1% being preferred.

In some applications, notably when this involves improving the sensitivity or reaction rate (without increasing the non-specificity of the test), a low ionic strength buffer ISB can be used, also called LISS buffer (LISS for low ionic strength solution).

The man skilled in the art will know that buffer or saline solution refers before to buffers commonly used in the field of cell biology, notably immunohaematology, in order to prevent lysis of red blood corpuscles, notably for IAR or phenotyping applications. Such buffers or solutions can be, for example, buffers at a physiological pH between 6.8 and 7.5 with the molarity of the buffer constituents being adjusted such that the final solution obtained is similar in terms of osmotic pressure to the molarity of an NaCl type solution at 9 per thousand (close to 0.15M NaCl). In particular, we can cite but without this being limiting PBS type phosphate buffer at pH 7.0-7.4, well known to The man skilled in the art.

The composition of ISB or LISS buffers will therefore not be described here as these buffers are well known in immunohaematology for their ability to boost agglutination reactions. These buffers are available from suppliers of reagents for hematology (for example, we can cite but without this being limiting a LISS buffer having the following composition, 16 g/l glycine, 0.03M NaCl and 0.015M phosphate at pH 6.7).

In a preferred embodiment, the present invention includes a method according to the invention wherein the reactor is a microplate cupule with a round base (also called a U-base or hemispherical base) or a V-shaped base.

Microplate cupule type reactors in which the base and inclined wall of the cupule is presensitised (coated) with human anti-immunoglobulin or any other compound capable of recognising an antibody can be easily obtained using techniques well known to the man skilled in the art (see in particular the examples below).

In a preferred embodiment, the present invention includes a method according to the invention characterised in that the antibody solution is a human plasma or serum sample wherein the objective is to detect the presence of an antibody directed specifically against an antigen bound to the magnetic particle, preferably an antibody that does not agglutinate with magnetic particles, in particular IgG type, and wherein the anti-immunoglobulin is a human anti-immunoglobulin, in particular human anti-IgG.

In a preferred embodiment, the present invention includes a method according to the invention wherein in step e), collection of magnetic particles at the lowest point in the reactor is characterised by the absence of the formation of a specific antibody/antigen complex or wherein the presence of at least a visible fraction of magnetic particles on the inclined wall of the reactor coated with the anti-immunoglobulin is characteristic of the formation of said complex.

Preferably, the magnetic particles can be stained for better visualisation of these particles.

In a preferred embodiment, the present invention includes a method according to the invention for demonstration of a specific complex formed by a reaction between an antibody present in the solution or an antigen carried by a cell or virus, itself bound to one or more magnetic particles (including the above-mentioned ferrofluid type solutions) depending on the size of the cell or virus and that of the particle.

Preferably, the cell is chosen from among eukaryotic, mammal or yeast cells, or bacteria.

Even more preferably, the cell is a mammal cell, notably human, preferably a white corpuscle, of the lymphocyte or macrophage type, or even a platelet or an erythrocyte (or red blood corpuscle).

In a particular aspect, the antigen carried by the cell is not an antigen that is naturally present at the external surface of the cell, this antigen being in this case previously fixed by covalent or ionic binding or adsorbed onto the surface of the cell.

In a preferred embodiment, the present invention includes a method according to the invention for demonstration of a specific complex formed by a reaction between the anti-antigen antibody of the blood group present in solution and an antigen of the blood group wherein the cell is an erythrocyte, and preferably wherein said antigen is a natural antigen carried by the erythrocyte.

In the present description, the terms "erythrocyte, red cell and red blood corpuscle" will be used interchangeably to designate the same blood cell.

In a preferred embodiment, the present invention includes a method according to the invention for irregular agglutinin research (IAR) or research of erythrocyte antibodies in a serum or plasma sample, preferably non-agglutinant antibodies, or even for red cell phenotyping wherein this includes a step in which erythrocytes carrying the antigen undergo preliminary binding by ionic bonds or adsorption to the magnetic particles or are in suspension in a ferrofluid solution, preferably the magnetic particles are non-functionalised and washed in the presence of surfactants, notably nonionic surfactants. These magnetic particles can, after washing in detergent, be contacted with an albumin solution (between 0.05 and 5%, preferably between 0.1% and 1%) in order to facilitate adsorption of the erythrocyte.

In this case, albumin is itself bound by ionic bonds or adsorbed onto the surface of the magnetic particle, if treatment of this particle or its functionalisation, notably its resulting surface charge, allows such ionic binding or adsorption, or even covalent coupling of albumin to groups on the magnetic particle, notably carboxylic or aldehyde groups grafted onto the surface of these particles allowing the formation of covalent bonds with the amine groups, in particular with the lysine residues of albumin (BSA).

In a preferred embodiment, the present invention includes a method according to the invention for red cell phenotyping wherein the antibody solution in step b) is a test serum solution containing an anti-antigen antibody of a known blood group, preferably of the IgG type, in which case the reactor is coated with an anti-immunoglobulin directed against the species providing the anti-antigen antibody of the blood group used (animal or human), or any other compound capable of recognising the specific antibody contained in this test serum (notably protein A or G).

In a preferred embodiment, the present invention includes a method according to the invention wherein before or after their binding to magnetic particles or suspension in a ferrofluid solution, preferably before, the erythrocytes can be subjected to the action of a protease, preferably bromelain or papain, this in order to encourage the formation of a specific complex, these blood phenotyping techniques being well known to the man skilled in the art.

In a preferred embodiment, the present invention includes a method according to the invention wherein the erythrocyte concentration in the final erythrocyte suspension bound to the magnetic particles or in the ferrofluid solution, prior to being added to the antibody solution in the reactor, is between 0.1% and 5% volume, preferably between 0.5% and 2.5% and between 0.75% and 2% volume, a value 1%±0.25% being the most preferred.

In a particularly preferred method of the invention for IAR and/or phenotyping carried out in a microplate cupule, this method includes the following steps:

a) prior to the reaction:
preliminary filling of a round-base cupule with 50 µl±10 µl of a homogeneous solution of superfine Sephadex™, G-100 gel at about 3%±0.5% in LISS type buffer in the presence of BSA at 10%±2.5% such that the inclined wall of the reactor is at least partially coated, and if need be,
addition of 60 µl±15 µl of LISS buffer at 3%±1% BSA, preferably at a pH between 6.5 and 7.55,
use of erythrocytes magnetised by means of a ferrofluid solution or magnetic particles, preferably in the case of magnetic particles of a size between 200 nm and 1000 nm or between 200 nm and 8.00 nm, these particles preferably being non-functionalised, preferably containing at least 40% ferrite (iron oxide), yet more preferably being coated with BSA and/or having been previously treated in order that these particles can bind ionically or by adsorption to the erythrocytes carrying the antigen capable of forming a specific with said antibody, notably by washing in a nonionic detergent, b) contacting, above the homogeneous gel solution or, if need be, above the LISS buffer at 3%±1% BSA, contained in the cupule,
the solution containing or likely to contain said antibodies with 25 µl±7.5 µl with the suspension of erythrocytes coated with magnetic particles carrying or likely to carry said antigen, the erythrocytes being at a concentration in suspension between 0.75% and 1.25% v/v, with
12 µl±8 µl of sample containing the antibodies (serum or plasma in the case of IAR, or test serum in the case of phenotyping), c) incubation of the reactor for 20 min±5 min at 37° C.±1° C., d) simultaneously, application of a magnetic field to said reactor and stirring of the reactor for a period of 5 min 30 s±1 min, and e) Reading with the naked eye and/or by any other appropriate reading system of the image obtained at the base of the reactor and/or the inclined wall of the reactor coated with said anti-immunoglobulin, the image obtained making it possible to demonstrate the presence or otherwise of the formation of a specific antibody/anti-antigen complex. Interpretation can be carried out with the aid of FIG. 3 and FIG. 4, respectively characteristic of a negative image (no formation of specific complex) and a positive image (presence of complex).

In another aspect, the object of the present invention is a device for the demonstration of a specific complex formed by reaction between an antibody present in solution and an antigen bound to a magnetic particle, preferably for the demonstration of a specific complex formed by reaction between an anti-antigen antibody of the blood group present in solution and an antigen of the blood group carried by the erythrocyte, itself bound to several magnetic particles, notably for IAR, investigation of erythrocyte antibodies, or even for blood group phenotyping wherein it includes;

a) a reactor or set of reactors with an open top and sealed base and whose diameter decreases at least in the zone close to the base in order to form an inclined wall extending down to the base, said inclined wall being at least partially coated with an anti-immunoglobulin or a compound capable of binding to the antibody of said formed complex,
each of the reactors can be partially filled with a viscous substance or gel, b) at least one magnet or set of magnets that can be arranged externally under the reactor(s) and a rotary stirring system of said reactor(s), where the stirring system preferably forms a single unit with the magnet or platform supporting the magnets in order to displace the magnets in the same way as the reactors during the stirring phase, c) if need be, an incubator capable of regulating the incubation temperature of reactors, and d) it need be, a reading system capable of evaluating the presence and localisation of magnetised erythrocytes at the end of the reaction in each of the reactors, notably on the inclined wall and base of the reactor coated with anti-immunoglobulin or compound capable of binding to the antibodies of the specific complex that may be formed.

Preferably, the device according to the invention is characterised in that the viscous substance or gel has the characteristics defined in the method according to the invention here and above with the same preferences. This is also true for the magnetic particles or suspension of magnetised cells, magnet and rotary stirrer characteristics.

Even more preferably, the device according to the invention is characterised in that said reactor is a microplate cupule, preferably with a round base (hemispherical) or V-shaped base, with a 96-cupule microplate being even more preferred.

Preferably, the magnet is in the form of a stack as shown in FIGS. 1A and 1B, preferably a platform consisting of 96 magnets in the form of a stack, each of which is placed under a cupule.

In yet another aspect, the invention relates to a kit formed for demonstration of a specific complex formed by reaction between an antibody present in a solution and an antigen bound to a magnetic particle wherein it includes:

a) a reagent including a suspension of magnetic particles coated with at least an antigen or to be coated with at least an antigen, and b) a reactor or set of reactors with an open top and sealed base and whose diameter decreases at least in the zone close to the base in order to form an inclined wall extending down to the base, said inclined wall being at least partially coated with an anti-immunoglobulin or a compound capable of binding to the antibody of said formed complex,
a container containing a viscous solution or a gel, or if need be, each reactor being partially filled with said viscous substance or said gel, and, c) if need be, at least one magnet or set of magnets which can be placed externally below the reactor(s), said magnets preferably forming an integral part of a rotary stirrer, preferably the stirrer's orbital being 2 mm±1 mm for a reactor diameter of 7 mm at its widest point (or in equivalent proportions).

Preferably the invention concerns a kit according to the invention for IAR characterised in that said reagent contains a suspension of test erythrocytes of known phenotype on which said magnetic particles adsorbed or coupled, or characterised in that it includes a second reagent containing a suspension of test erythrocytes of known phenotype for adsorption or coupling to the magnetic particles or ferrofluids contained in the same reagent.

Preferably the invention relates to a kit according to the invention for phenotyping blood groups characterised in that said reagent contains a test serum containing an anti-antigen antibody of the blood group, preferably of the IgG type, and in addition, a reagent containing a suspension of magnetic particles or ferrofluid solution capable of binding to the erythrocyte suspension whose phenotype is being researched.

Also preferably, the invention relates to a kit according to the invention characterised in that the viscous substance or gel, and if needs be the magnetic particles or suspension of magnetised cells, if needs be the characteristics of magnet and rotary stirrer, have the characteristics defined for the method according to the invention with the preferences specified for these viscous solutions or gel or other compounds and elements.

Preferably still, the invention relates to a kit according to the invention characterised in that said reactor is a microplate cupule, preferably with a round base (hemispherical) or V-shaped based, the microplate consisting of 96 cupules being the most preferred.

The figures and headings below as well as the examples are intended to illustrate the invention without limiting its extent in any way.

FIGURES

FIGS. 1A and 1B; diagram of the view from above (FIG. 1A) and view from the side (FIG. 1B) of the stirring platform Teleshake™) consisting of a soft iron plate under the microplate under which the soft iron plate each magnet is fixed magnetically in the form of a stack under each of the microplate cupule.

(1) Plastic spacer making it possible to obtain good spacing between magnets; (2) Elements making it possible to wedge the microplate on Teleshake; (3) Teleshake wedge making it possible to wedge the microplate; (4) Stack magnets; (5) Microplate; (6) Plastic spacer; (7) Mild iron plate on which magnets are magnetically fixed; (8) Cardboard plate isolating Teleshake from the magnetic field of the magnet stack; (9) Teleshake rotary tray.

FIGS. 2A and 2B: Diagrams of a round based (or U-shaped) reactor cupule after coating with anti-immunoglobulin on the inclined wall (partially) and the base of the cupule prior to addition of the gel solution (buffer 1) and various solutions and reagents.

Figure 3:
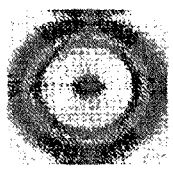

FIG. 3: Photograph showing an image of a negative immunoadhesion reaction with antigens carried by the erythrocyte (no formation of specific complex).

Figure 4:

FIG. 4: Photograph showing an image of a positive immunoadhesion reaction with antigens carried by erythrocytes (formation of specific complex adhering to the inclined wall coated with anti-immunoglobulin).

Figure 5:
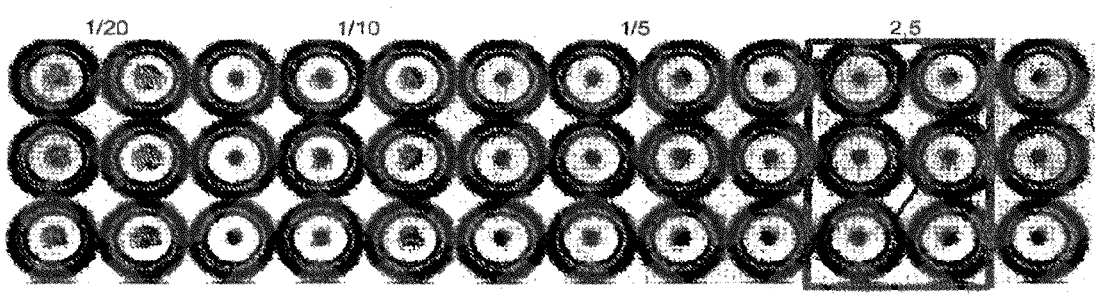

FIG. 5: Titration of CNRGS anti-D, polycontrol dilution, doubtful at 1 cross on homozygous red blood corpuscles at 2.5 ng/ml.

Figure 6:
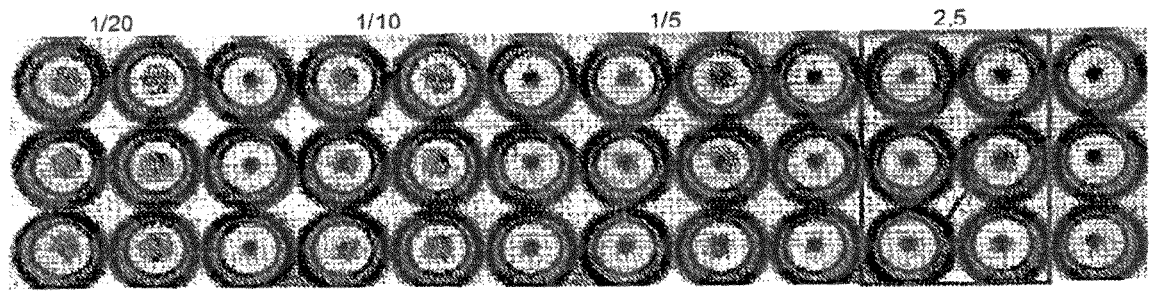

FIG. 6: Titration of CNRGS (French National Reference Centre for Blood Group3), anti-D, dilution in AB plasma, 1 cross on homozygous red blood corpuscles at 2.5 ng/ml.

Figure 7:
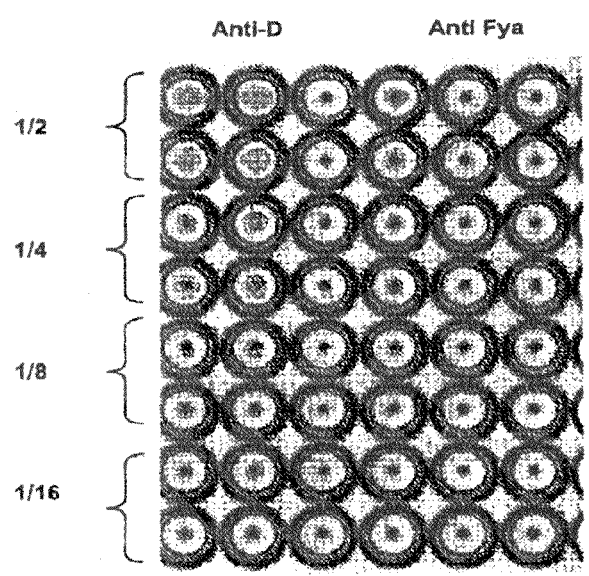

FIG. 7: Titration of quality controlled anti-D and anti-FYA in AB serum*

Figure 8:
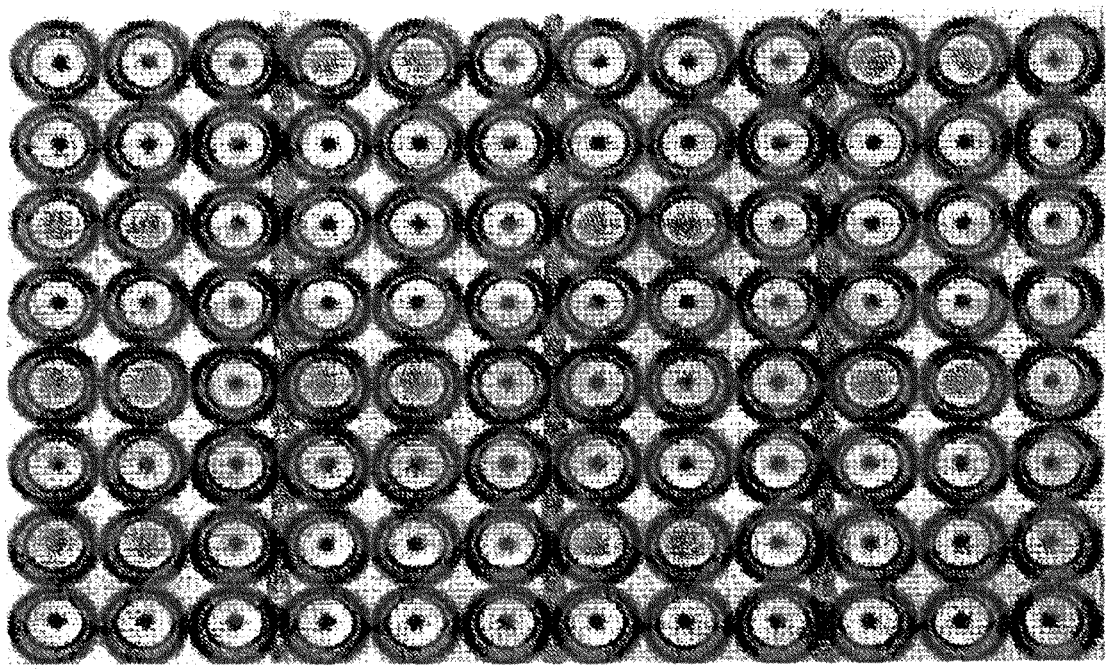

FIG. 8: Repeatability and reproducibility 5 8 negative samples and 4 positive samples (anti-D) were passed 3 times on the same plate.

Figure 9:
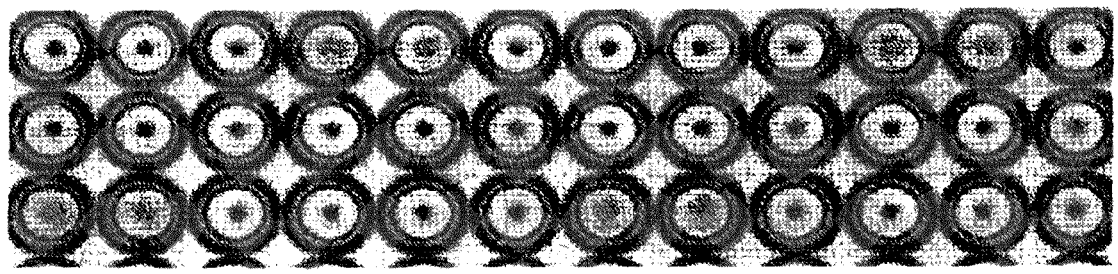

FIG. 9: Repeatability and reproducibility.

8 negative samples and 4 positive samples (anti-D) were passed over another plate.

Figure 10:
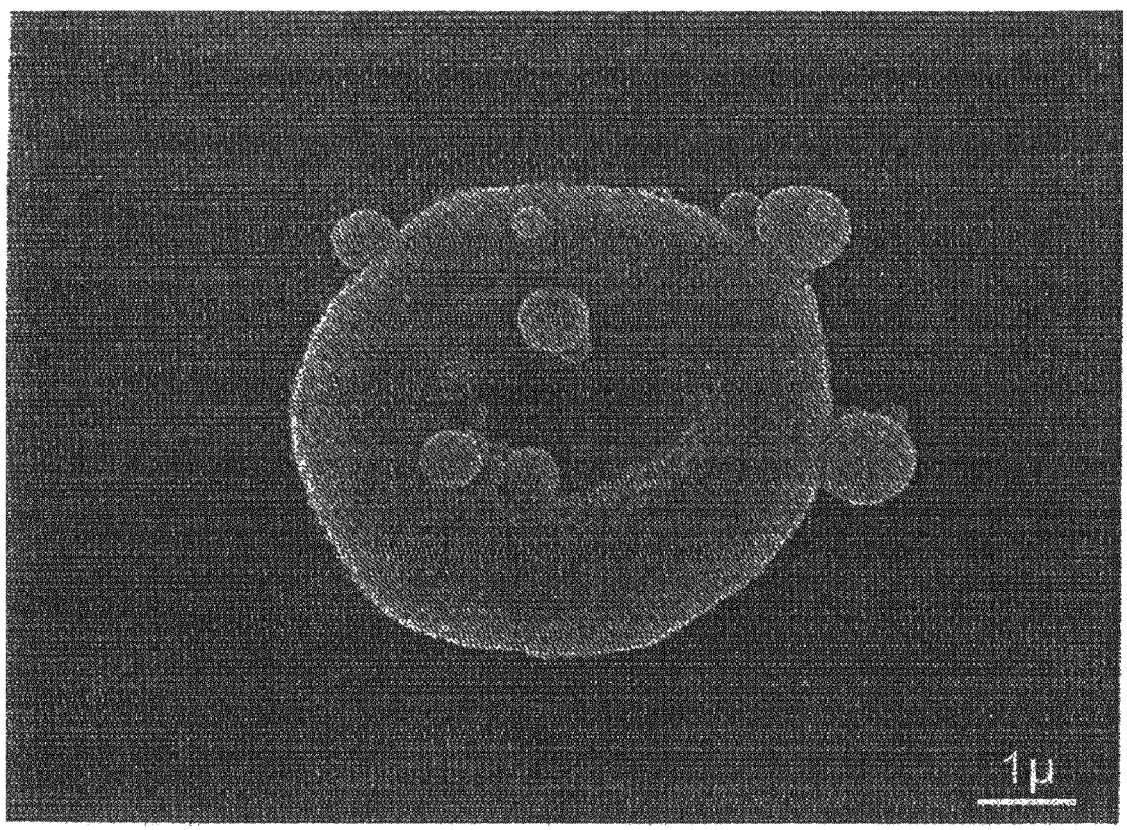

FIG. 10: Electron microscopy photograph of a Hemascreen™ red blood corpuscle magnetised using magnetic particles with an average diameter of 500 to 750 nm, ready to use.

Figure 11:
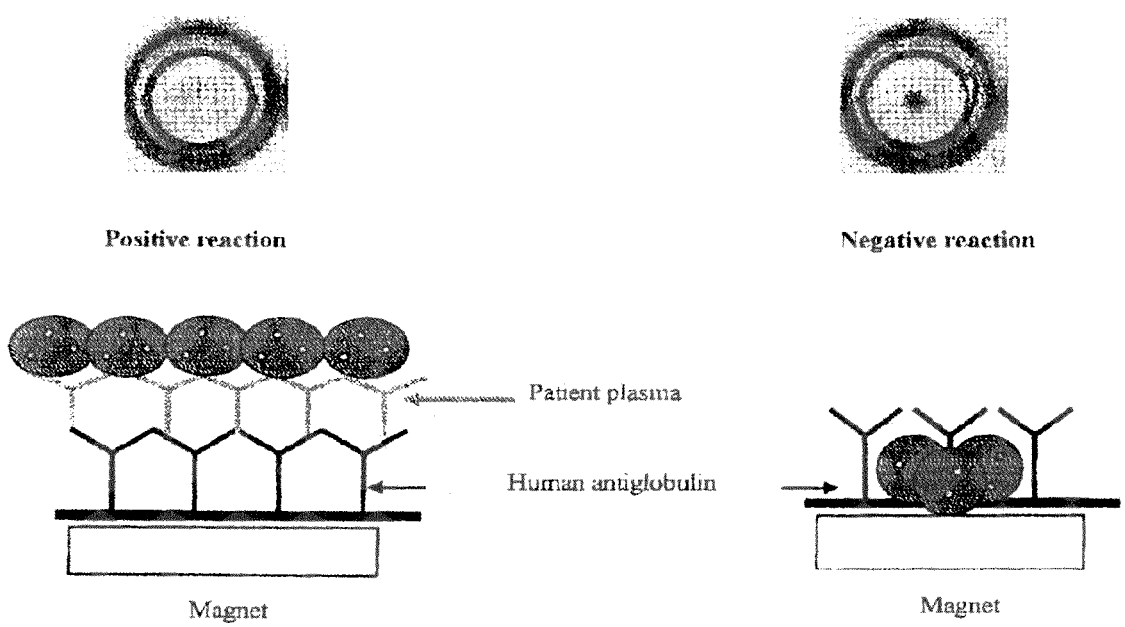

FIG. 11: results obtained in a microplate cupule for evaluation of the sensitivity of the Qwalys™ IAR method in a test anti-RH1 sample (international reference)

Figure 12:
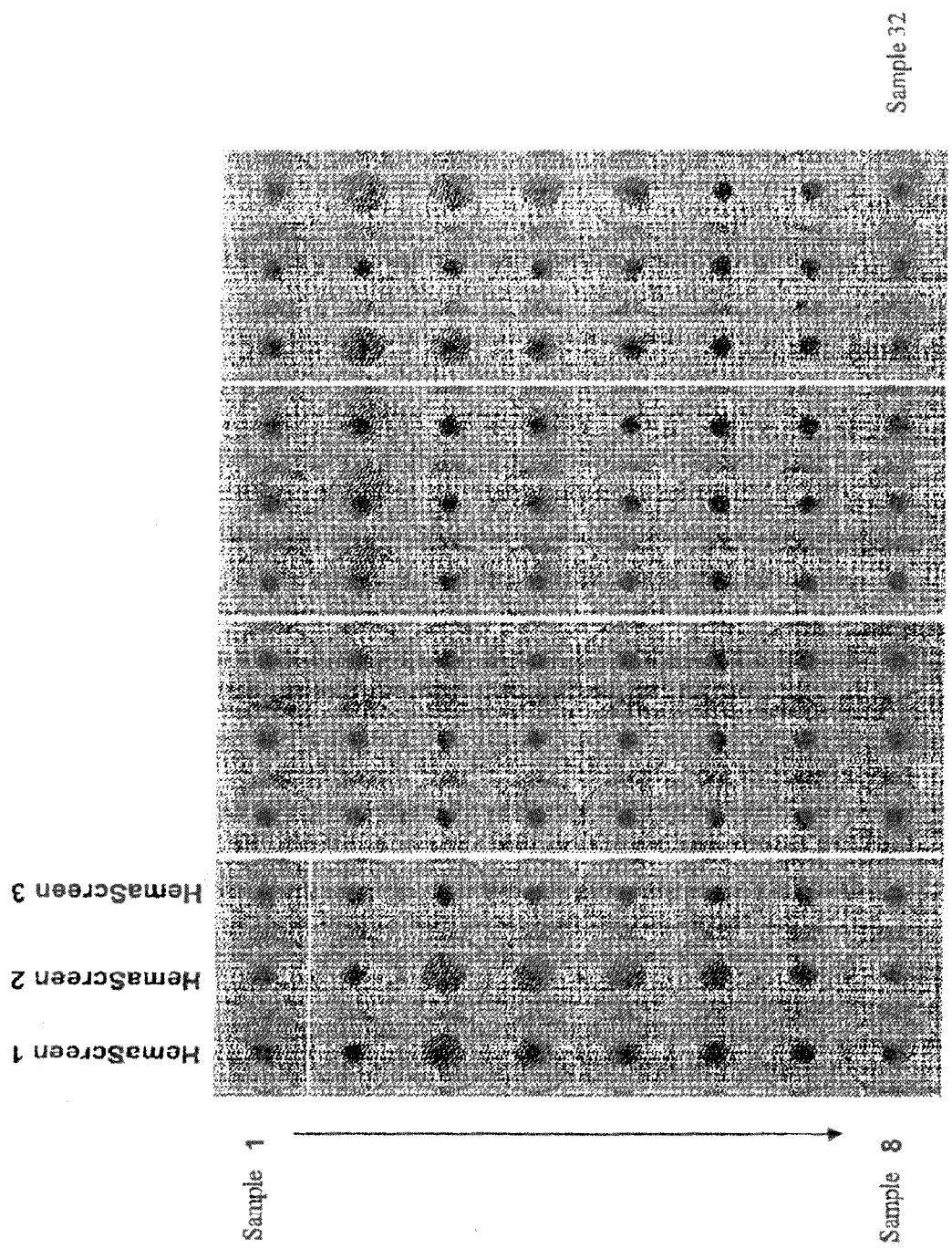

FIG. 12: Typical results obtained for a microplate cupule for IAR in patients plasma or serum samples with a panel of 3 red blood corpuscles according to the Qwalys™ technology of the invention.

Figure 13:
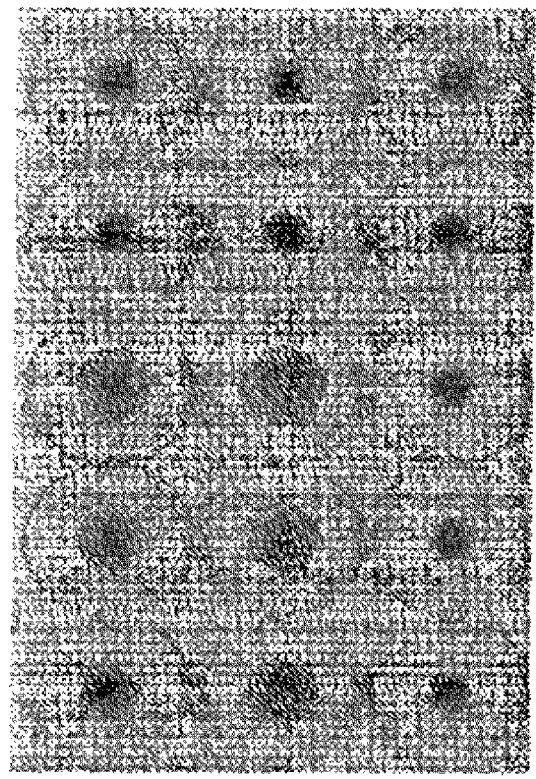

FIG. 13: Results obtained in a microplate cupule for evaluation of the sensitivity of the Qwalys™ IAR method in an anti-RH1 test sample (international reference)

EXAMPLE 1

Coating of the Inclined Wall and Cupule Base with an Anti-Immunoglobulin

The chemical and physico-chemical nature of the plastic used for the cupules makes it possible to cover the latter with a layer of human anti-immunoglobulin (monoclonal or polyclonal HAG type) capable of specific binding to the antibodies of any specific complexes that may be formed when the antibody of said complex is of human origin.

Moreover, it can be noted that this HAG composition can include antibodies directed against complement-type serum protein determinants.

The surfaces of the internal wall of the container which are not coated with HAG can be saturated using conventional saturating agents in solid phase or ELISA (Enzyme Linked Immunosorbent Assay) type techniques.

For example, the HAG solution at a concentration of 1 to 10 µg/ml can be prepared in a 0.2M carbonate buffer pH 9.6.

This solution is distributed at a volume of 75 µl in each cupule of a round-based Maxisorp NUNC U8 type microplate. The plates are then incubated overnight at 4° C.

The cupules are then washed using a phosphate buffer solution (PBS 10 2.5 mM, pH 7.4) in order to eliminate any proteins not directly adsorbed onto the plastic.

The cupules 1 are then treated with an albumen solution at 30 g/l in PBS buffer at a rate of 100 µl per cupule.

After incubation for 2 hours at room temperature, the cupules are washed again in phosphate buffer.

EXAMPLE 2

Preparation of a Suspension of Erythrocytes Magnetised by Means of Magnetic Particles or a Ferrofluid Solution A) Using Magnetic Particles In this example, we used paramagnetic particles showing great homogeneity of size (about 300 nm diameter), a high ferromagnetic material charge (greater than 50% by weight, about 75% by weight) and a fairly hydrophobic surface condition (non-functionalised). These particles can be used directly for the magnetisation of erythrocytes, or preferably after preliminary washing in a non-ionic detergent.

These particles can also be used after a step in which they are treated with bovine serum albumen (BSA) to bind Perythrocytes such that multiple weak bonds are created between the surface of Perythrocyte and the particle.

Binding takes place in two stages. The first stage consists of activating the particles with BSA while the second stage involves contacting these magnetic particles coated with BSA with a suspension of erythrocytes that may or may not be treated by proteolytic enzymes.

The erythrocytes obtained in this way are drawn by a magnetic field and can thus be used in the method of the invention.

a) First Step, Activation of Ferromagnetic Particles with BSA.

Ademtech type non functionalised hydrophobic particles of about 300 nm undergo preliminary washing and storage in a non-ionic detergent.

If necessary, these particles are contacted with a 0.1% bovine albumen (weight/volume) solution in PBS butter pH 7.2. After incubation for 30 minutes at room temperature and with non-magnetic stirring, the particles in suspension are drawn by the magnet and the particle-free supernatant is eliminated. The residue of particles coated with BSA can then be used directly for the erythrocyte magnetisation step.

b) Second Step, Magnetisation of Erythrocytes

The globular suspension placed in LISS buffer at a suitable concentration (possibility of carrying out erythrocyte magnetisation with cell suspensions between 0.6 and 10% v/v and, if need be, previously washed 3 times with saline solution for example) is added to the ferromagnetic particle residue obtained in the previous step. After carrying out full homogenisation, the suspension is incubated for 30 minutes at room temperature with gentle and even stirring. The erythrocytes are then washed in PBS buffer pH 7.4 (two washings per centrifugation, 3 minutes at 500 g). The magnetised erythrocyte residue can then be taken up at the concentration to be used in the analysis by means of LISS type (or BFI type) buffer.

In a particular example, the ratio of the quantity of particles used and quantity of erythrocytes is between 10 and 30, such that effective magnetisation is obtained without risking the degradation of blood group antigens present at the surface of the erythrocytes.

The erythrocytes obtained in this way can either be used directly as a reagent (for IAR for example) or as an analyte (for phenotyping). At this stage, they can also undergo treatment with proteolytic enzymes such as bromelain or papain if necessary in order to perform the required analysis.

B) Using a Ferrofluid Solution
1) Manufacture of Pre-Purified Ferrofluid
Materials and Method
Special Materials and Products
   1 filter, Stericup GS 200 ml 0.22 μm (Ref.: 107943)
   1 magnet
   28-30% $NH_4OH$ solution (ACROS, Ref.: 205840025)
   60% $HNO_3$ solution (NORMAPUR, Ref.: UN 2031)
   $FeCl_2$, $4H_2O$ (SIGMA, Ref.: 22, 029-9)
   $FeCl_3$, $6H_2O$ (SIGMA, Ref.: F-2877)
Manufacture of Ferrofluid:
Preparation:

1/ Weigh 13.51 g of $FeCl_3$ and dissolve in 20 ml of filtered demineralised water by means of magnetic stirring. Transfer the solution to a 50-ml test tube, rinse and adjust the volume to 50 ml with filtered demineralised water (1 M solution).

2/ Weigh 19.88 g of $FeCl_2$ and dissolve in 20 ml of filtered demineralised water by means of magnetic stirring. Transfer the solution into a 50-ml test tube, rinse and adjust the volume to 50 ml with filtered demineralised water (2 M solution).

3/ Filter each solution on a 0.22 μm syringe filter.

4/ Place 30 ml of a 28% ammoniac solution ($NH_4OH$) in a 250-ml test tube and add qsp for 120 ml filtered demineralised (2 M solution).

5/ Weigh an empty Rotavapor 1 L glass flask.
Incubation:

6/ Place 10 ml of $FeCl_2$ solution (2 M) and 40 ml of $FeCl_3$ solution (1 M) in a 1 L Rotavapor flask and homogenize the solution by stirring the flask 25 manually.

7/ Add 200 ml of filtered demineralised water and homogenize the solution by stirring the flask manually.

8/ Place the flask at an angle in a Rotavapor type apparatus.

9/ Rotate the flask at maximum speed to homogenize the solution well.

10/ Add 120 ml of 2 M ammoniac solution.

11/ Rotate the flask for 15 minutes.

12/ Place 105 ml of 60% nitric acid $HNO_3$) in a 1 L flask and add qsp 1 L of filtered demineralised water (1 M solution).

13/ After 15 minutes of rotation, place the flask on the magnet for 4 minutes.

14/ Aspirate the totality of the supernatant.

15/ Resuspend the residue.

1st Washing:

16/ Place the flask on the Rotavapor and rotate at maximum speed.

17/ Add 200 ml of 1 M $HNO_3$ solution.

18/ Rotate the flask for 10 minutes.

19/ Resuspend the residue.

20/ Repeat this process until the residue is completely dissolved.

21/ Place the flask on [missing word in Fr text] in order to decant the iron suspension.

22/ Aspirate the supernatant.

23/ Resuspend the residue.

Steps 16 to 23 can be repeated if necessary.
Final Dilution:

26/ Weigh the flask.

27/ Deduce the residue weight obtained and calculate reaction yield:

$$(\text{Residue weight obtained}/\text{Initial iron weight}) \times 100$$

Initial iron weight=14.77 g
55%<yield

28/ Add 200 ml of filtered water to the flask.

29/ Place the flask on a Rotavapor.

30/ Resuspend the residue.

31/ Filter the solution on a 0.22 μm Stericup filter.
Preparation of the Ferrofluid Stock Solution:

Dilute the ferrofluid obtained above in LISS buffer or saline solution to the desired concentration in a bottle. Store the ferrofluid and/or dilute solution at 4° C.

2) Magnetisation of Erythrocytes
a) Possibility 1:
   contacting the erythrocytes with the ferrofluid solution diluted to 0.3 to 0.5% (v/v) in LISS or saline solution in order to obtain the desired erythrocyte concentration in the final suspension, preferably between 0.5% and 3% of erythrocytes.
b) Possibility 2:
   adjust the ferrofluid solution to an OD value at 450 nm equivalent to 0.9 in LISS,
   add 10 μl of globule residue at 80% haematocrit per 240 μl of ferrofluid solution.

EXAMPLE 3

Example of the Protocol, Materials and Methods for IAR

A) Protocol

1. Use a 96-well microplate coated with HAG (Human Anti-Globulin)
2. Deposit 50 µl of Buffer 1 (gel solution) in as many cupules as needed for the IAR test.
3. Deposit 60 µl of LISS solution at 3% in BSA per cupule.
4. Deposit 12 µl of sample (serum or plasma) to be analysed.
5. Deposit 25 µl of IAR panel magnetised red blood corpuscles (red blood corpuscle 1 in well 1, red blood corpuscle 2 in well 2, red blood corpuscle 3 in well 3).
6. Incubate the microplate during 20 min at 37° C.
7. Remove the microplate from the incubator.
8. Place the plate on Teleshake™ (microplate stirrer supplied by H+P LAB., Germany) adapted to the needs of this protocol (see FIGS. 1A and 1B).
9. Stir for 5 min 30 sec. at 500 rpm.
10. Read Coated plates (with HAG) before and after deposit (see FIGS. 2A and 2B).

B) Readings (Viewed from Above) (See FIGS. 3 and 4)

1. A central residue, regular and smooth, is read as negative (see FIG. 3).
2. Any opening in the central residue is considered to be positive.
3. A cell layer over the surface of the wells is interpreted as a strong positive (see FIG. 4).

C) Composition of the Elements Needed for the Reaction

1. Butter 1
1.1. Adjust 30% BSA to a concentration of 10% in LISS Buffer.
1.2. Weight out superfine Sephadex™ G-100 (600 mg per 20 ml of buffer 1) (Ref. 17.0061.01-Amersham Bioscience).
1.3. Dissolve the Sephadex™ in BSA previously adjusted to 10% in LISS.
1.4. Leave buffer 1 overnight at 4° C. before using.
2. 3% LISS solution in BSA (see composition of a LISS type solution in the description) or use a commercially available LISS solution.
3. LISS buffer (see composition in the description).
4. IAR panel magnetised red blood corpuscles (see Example 2).
5. Microplate coated with anti-immunoglobulin.

Maxisorp NUNC microplate with 96 wells coated with 1 to 5 µg/ml of Human monoclonal anti-IgG antiglobulin (see previous example for coating conditions).

EXAMPLE 4

Results

A) Study of Recipients

The protocol was tested on 308 recipient samples.

Red blood corpuscle panel magnetised 15 days prior to the commencement of tests.

TABLE 1

Comparison with a standard technique (Diamed) by gel centrifugation

| IAR | | METHOD OF THE INVENTION | | | |
|---|---|---|---|---|---|
| | | Positive | Doubtful | Negative | TOTAL |
| DIAMED | Positive | 4 | 0 | 0 | 4 |
| | Negative | 3 | 2 | 299 | 304 |
| TOTAL | | 7 | 2 | 299 | 308 |

Only 5 out of 308 samples were at variance, i.e. 98.4% concordance with Diamed.

All positive samples were read by the method of the invention.

Sensitivity 100% (n=4)

Among the 304 negative results, 5 were at variance, i.e. 98.3% correlation

| | |
|---|---|
| Level of real false positives: | 1% |
| Level of doubtful results: | 0.6% |
| Specificity (n = 304): | 98.3% |

B) Study of Positive Panels

1) First panel tested, 22 positive serums,
7 serums with their dilutions, two serum samples with anti-D antibodies, two samples with anti-Fya antibodies, one with anti-Kell antibodies, one with anti-E antibodies and one with anti-S.

Results: no failed sample.

2) Second Panel (Life Therapeutics)
32 serums

TABLE 2

| Antibodies | Number of samples |
|---|---|
| CDE | 2 |
| C | 3 |
| D slide | 5 |
| e | 2 |
| Fya | 4 |
| Jkb | 3 |
| Fyb | 2 |
| Jka | 1 |
| Kpb | 2 |
| S | 2 |
| Lub | 1 |
| E | 3 |
| Jsa | 1 |
| Lua | 1 |

Panel tested with the protocol of the invention (described in the examples))

Results; no failed positive serum.

Only 2 samples out of the 3 red blood corpuscles tested by screening did not show full concordance, 2 red blood corpuscles were false positives.

3) Recipient Test at Lille Regional Teaching Hospital (CHR&U de Lille, France)

4 recipient samples at Lille CHR&U were detected as positive by our method and confirmed by the DIAMED reference method.

4) Detection Threshold

Protocol of the Invention

In order to test the detection threshold of the described method, we used anti-D at 20 ng/ml from CNRGS (French National Reference Centre for Blood Groups) as well as a control quality anti-Fya antibody, both diluted in polycontrol.

CNRGS Anti-D

Dilution in polycontrol: doubtful at 1 cross on homozygous red blood corpuscles at 2.5 nq/ml.

See FIG. 5

Dilution in AB plasma: 1 cross on homozygous red blood corpuscles at 2.5 ng/ml.

See FIG. 6

Titration of quality control anti-D and anti-Fya in AB serum

See FIG. 7

5) Repeatability and Reproducibility

Protocol of the Invention

To test the protocol, 8 negative samples and 4 positive samples (anti-D) were passed through 2 different plates and 3 times on the same plate.

3 times on the same plate (intra-plate test) (see FIG. 8).

on another plate (inter-plate test to be compared with FIG. 8) (see FIG. 9).

The results observed demonstrate the excellent reproducibility and repeatability of the invention.

EXAMPLE 5

Evaluation of the Sensitivity of the IAR Method According to the Invention (Called Qwalys™) Compared to DiaMed™ Technology and the Standard Anti-Globulin LIS Tube Technique (<<LISS Tube>>)

A) Magnetisation of Red Blood Corpuscles

Coupling by Passive Adsorption of Red Blood Corpuscles to Magnetic Particles

Method:

Non-functionalised magnetic polystyrene particles, with a diameter of 500 nm to 1 μm and capable of containing about 30 to 70% ferrite on average, were used here (type, Estapor™, Merck-Chimie S.A.S./Estapor Microspheres, Fontenay-Sous-Bois, France, or Ademtech, Pare Scientifique Unitec 1, 4 Allée du Doyen Georges Brus 33600 Pessac, France).

These polystyrene particles can, depending on the proposed model, for example in the Estapor™ or Ademtech range, contain between 10 and 70% ferrite or iron oxide and have diameters ranging from 300 nm to 1 300 nm on average, depending on the model chosen.

The magnetic particles, generally supplied at 10% (w/w), were adjusted to 1% (10 mg/ml) with the dilution buffer for red blood corpuscles, preferably an adsorption buffer such as LIS type buffer (low ionic strength).

Particles can undergo preliminary washing in this buffer or in PBS buffer, if need be, prior to dilution in order to remove any trace of detergent prior to contact with red blood corpuscles.

A suspension of test red blood corpuscles at 1% in LIS was contacted with the 1% magnetic particle suspension and the mixture was stirred gently (see FIG. 10 for an electron microscopy image of a ready-to-use magnetised red blood corpuscle obtained in this way).

Although passive adsorption essentially takes place within a few minutes, contact can be prolonged up to 30 minutes, and even 1 to 2 hours at 20 temperatures ranging from 4° C. to 37° C., or even overnight or longer at 4° C., if necessary, prior to use.

B) IAR Protocol without Washing or Centrifugation in Human Anti-Globulin Coated Cupule Microplates with Ready-to-Use Magnetised Red Blood Corpuscles.

1—Add 50 μl of a gel solution (<<Buffer 1>> also called Nanolys™) of the superfine Sephadex™ G-100™ type at 3% in a solution of 10% albumin in LIS to each U-shaped microplate couple coated with human antiglobulin (Microplate coated with antiglobulin, called ScreenLys™).

2—Add 60 μl of LISS solution at 3% in BSA (called ScreenDiluent™).

3—Add 12 μl of sample (serum or plasma) to be analysed and 25 μl of red blood corpuscles 4—magnetised on an IAR panel (called Hemascreen™) over ScreenDiluent™. Incubate the ScreenLys™ microplate obtained in this way for 20 min at 37° C.

5—After incubation, place the microplate on a magnetic stirrer for about 5 minutes.

6—Read the results with the naked eye or using an automated reader (see FIGS. 11 and 12 for readings and typical results obtained on a Hemascreen™ panel of 3 red blood corpuscles 1, 2 and 3).

C) Results

TABLE 3

Comparative sensitivity of the 3 techniques expressed as the titre (2 in 2 dilution) of the specific antibodies detected

| Antibody specificity | QWALYS ™ titre | DiaMed ™ titre | <<LISS tube>> titre |
|---|---|---|---|
| Anti-D | 8 | 4 | 4 |
| Anti-D | 4 | 4 | 16 |
| Anti-c | 8 | 4 | 8 |
| Anti-c | 16 | 8 | 8 |
| Anti-E | 16 | 64 | 16 |
| Anti-e | 8 | 4 | 4 |
| Anti-K | 2 | 2 | 2 |
| Anti-Fy$^a$ | 16 | 8 | 4 |
| Anti-Fy$^a$ | 8 | 2 | 8 |
| Anti-Jk$^a$ | 8 | 16 | 8 |
| Anti-Jk$^a$ | 4 | ? | 4 |
| Anti-S | 4 | 8 | 2 |
| Anti-S | 8 | 8 | 4 |

TABLE 4

Study of the comparative sensitivity of 2 techniques (Qwalys ™ and DiaMed ™) for a specific antibody panel

| Specificity | Number | QWALYS ™ | DiaMed ™ |
|---|---|---|---|
| Anti-D | 26 | 26 | 22 |
| Anti-E | 10 | 8 | 9 |
| Anti-c | 6 | 6 | 6 |
| Anti-e | 1 | 1 | 1 |
| Anti-K | 12 | 10 | 12 |
| Anti-Fy$^a$ | 10 | 10 | 10 |
| Anti-Jk$^a$ | 5 | 5 | 5 |
| Anti-Jk$^b$ | 1 | 1 | 0 |
| Anti-S | 1 | 1 | 1 |
| Anti-s | 1 | 1 | 1 |
| Anti-Lu$^b$ | 2 | 2 | 2 |
| Samples with a mixture of antibodies | 16 | 16 | 16 |
| Total | 91 | 87 | 85 |
| % positive | | 95.6 | 93.4 |

TABLE 5

Study of the comparative sensitivity of the 3
techniques (Qwalys ™, DiaMed ™ and <<LISS
tube>>) in a donor or antenatal sample panel

| Number of samples | QWALYS ™ Positive | DiaMed ™ Positive |
|---|---|---|
| 1590 | 32 (2.01%) | 24(1.51%) |
| Number of positives with the LISS tube (with antiglobulin) | 16 | 16 |
| Specificity | 98.99% | 99.5% |

EXAMPLE 6

Evaluation of the Sensitivity of the IAR Technique According to the Method of the Invention (Qwalys™) Compared to DiaMed™ Technology in a International Reference Test Sample An international standard for evaluation of the sensitivity of IAR methodology is used here.

This is a sample with anti RH1 antibodies (from the National Institute for Biological Standards and Control, CB).

The detection threshold found is close to 0.014 IU/ml for Qwalys™ technology according to the invention using magnetised red blood corpuscles, sensitivity that is identical to that found with the DiaMed™ technique (see FIG. 13).

CONCLUSION

The comparative study of Qwalys™ washing free and centrifugation free technology for IAR using magnetised red blood corpuscles and a stirring step in the presence of a magnetic field (magnetic stirring) according to the present invention confirms that this new technology shows specificity and sensitivity 10 that is equivalent to that of <<gel with centrifugation>> technology (DiaMed™), one of the standard TAR techniques.

One of the great advantages of the new Qwalys™ technology according to the invention, notably compared to DiaMed™ technology requiring a centrifugation step, is that it can be easily automated compared to other techniques as it does not involve a washing step (and therefore sample transfer) or centrifugation step (a step which limits the possibility of complete automation).

The invention claimed is:

1. Method for the demonstration of a specific complex formed by reacting an antibody present in a solution and an antigen bound to a magnetic particle, the reaction taking place in a reactor with an open top and sealed base whose diameter decreases in the area close base to the base in such a way that it forms an inclined wall extending down to the base, said inclined wall being at least partially coated with an anti-immunoglobulin or any other compound capable of binding to the antibody of said formed complex, wherein it consists of the following steps:
 a) prior to the reaction,
 preliminary filling of the reactor with a viscous substance or homogeneous gel such that at least part of the inclined wall of the reactor is coated,
 b) contacting the solution containing or likely to contain said antibody with the magnetic particle suspension carrying or likely to carry said antigen at a point above the viscous solution in the reactor,
 c) incubation of the reactor, preferably for the period of time and temperature required for the formation of the complex,
 d) application of a magnetic field to said reactor and stirring of the reactor such that the magnetic particles are either drawn towards the base and/or inclined wall of the reactor, and
 e) reading with the naked eye and/or by any other suitable reading system of the image obtained at the base of the reactor and/or inclined wall of the reactor coated with said anti-immunoglobulin or any other compound capable of binding to the antibody, the image obtained making it possible to demonstrate the presence or otherwise of a specific antibody/antigen complex.

2. Method according to claim 1 characterised in that the reaction mixture obtained by mixing the solution containing or likely to contain said antibody and the magnetic particle suspension carrying or likely to carry said antigen contains one or more antibodies not directed against the antigens carried by the magnetic particles and capable of binding to the anti-immunoglobulin or to any other compounds capable of binding to the antibody.

3. Method according to claim 1 or 2 characterised in that in step d), application of a magnetic field to said reactor and reactor stirring are carried out simultaneously.

4. Method according to one of claims 1 to 3 characterised in that in step d), application of a magnetic field and stirring are carried out simultaneously for a period of 2.5 min to 10 min.

5. Method according to claim 4 characterised in that in step d), application of a magnetic field and stirring are carried out simultaneously for period of 5 min to 6 min.

6. Method according to one of claims 1 to 5 characterised in that in step d), application of a magnetic field is carried out by means of a magnet located externally below the reactor such that the magnetic particles are drawn towards the base of the reactor.

7. Method according to claim 6 characterised in that in step d), said magnet is a permanent magnet of magnitude ranging from 10,000 to 14,000 Gauss.

8. Method according to one of claims 1 to 7 characterised in that in step d), stirring is carried out by means of a rotary stirrer.

9. Method according to claim 8 characterized in that in step d), stirring is carried out at a rate between 250 and 750 rpm.

10. Method according to one of claims 1 to 9 characterised in that in step c), the duration of incubation is between 10 min and 30 min.

11. Method according to one of claims 1 to 10 characterised in that in step c), incubation is carried out at a temperature between 20° C. and 40° C.

12. Method according to one of claims 1 to 11 characterised in that in step b), incubation is carried out at a temperature of 37° C.+1° C.

13. Method according to one of claims 1 to 12 characterised in that the magnetic particles have a diameter between 100 nm and 1.5 μm.

14. Method according to one of claims 1 to 13 characterised in that the magnetic particles contain at least 40% by weight of ferromagnetic compounds.

15. Method according to one of claims 1 to 14 characterised in that in step a), preliminary filling of the reactor with a viscous substance or homogeneous gel is carried out using a viscous substance or gel whose density is such that it prevents the migration of antibodies which do not form complexes with the antigens bound to the magnetic particles towards the inclined wall and the base of the reactor coated with anti-immunoglobulin or any other compound capable of binding to the antibodies during step d).

16. Method according to one of claims 1 to 15 characterised in that in step a), the viscous solution or gel has a density greater than 1.

17. Method according to one of claims 1 to 16 characterised in that in step a), the gel is a dextran or agarose gel.

18. Method according to one of claims 1-17 characterised in that in step b), the solution containing or likely to contain said antibody is deposited on the viscous solution prior to depositing the magnetic particle suspension carrying or likely to carry said antigen.

19. Method according to one of claims 1-17 and 18 characterised in that prior to step b), the viscous solution or gel is coated with an aqueous solution intended for dilution of the reaction mixture deposited in step b).

20. Method according to one to one of claims 1-17 and 18-19 characterised in that prior to step b), the viscous solution or gel is coated with an aqueous solution intended to encourage the formation of antigen/antibody complex in step b).

21. Method according to one of claims 1-17 and 18-20 characterised in that the reactor is a microplate cupule with a round or V-shaped base.

22. Method according to claim 21 characterised in that in step d), stirring is rotary stirring with an orbit between 1.0 mm and 2.5 mm in diameter.

23. Method according to claim 22 characterised in that the antibody solution is a human plasma or serum sample wherein demonstration of the presence of an antibody directed specifically against an antigen bound to the magnetic particle is being researched and wherein the anti-immunoglobulin is a human anti-immunoglobulin.

24. Method according to one of claims 1-17 and 18-23 characterized in that in step e), collection of magnetic particles at the lowest point in the reactor is characterised by the absence of the formation of a specific antibody/antigen complex or wherein the presence of at least a visible traction of magnetic particles on the inclined wall of the reactor coated with the anti-immunoglobulin is characteristic of the formation of said complex.

25. Method according to one of claims 1-17 and 18-24 for demonstration of a specific complex formed by a reaction between an antibody present in a solution or an antigen carried by a cell itself bound to one or more magnetic particles.

26. Method according to claim 25 for demonstration of a specific complex formed by a reaction between the anti-antigen antibody of the blood group present in a solution and an antigen of the blood group wherein the cell is an erythrocyte.

27. Method according to claim 26 for irregular agglutinin research (IAR) in a serum or plasma sample wherein it includes a step in which the erythrocyte suspension carrying the antigens is bound by adsorption to the magnetic particles previously contacted with an albumin solution.

28. Method according to claim 26 for phenotyping red cells wherein the antibody solution in step b) is a test serum solution containing an anti-antigen antibody of a known blood group.

29. Method according to claim 28 characterised in that prior to binding of the magnetic particles, the erythrocytes are subjected to the action of a protease.

30. Method according to one of claims 26 to 29 characterised in that the erythrocyte concentration in the suspension containing erythrocytes bound to magnetic particles is between 0.1% and 5%.

* * * * *

UNITED STATES PATENT AND TRADEMARK OFFICE
CERTIFICATE OF CORRECTION

| | | |
|---|---|---|
| PATENT NO. | : 8,093,067 B2 | Page 1 of 1 |
| APPLICATION NO. | : 12/084507 | |
| DATED | : January 10, 2012 | |
| INVENTOR(S) | : Yves Barbreau et al. | |

It is certified that error appears in the above-identified patent and that said Letters Patent is hereby corrected as shown below:

In the Claims, Column 25, Claim 1, line 54, please delete "close base to" and insert -- close to --.

Column 26, Claim 12, line 54, please delete "37°C.+" and insert -- 37°C+ --.

Signed and Sealed this
Twenty-fifth Day of September, 2012

David J. Kappos
*Director of the United States Patent and Trademark Office*